United States Patent [19]

Halskov

[11] Patent Number: 4,496,553
[45] Date of Patent: Jan. 29, 1985

[54] PHARMACEUTICAL COMPOSITION AND METHOD FOR THE TREATMENT OF COLITIS ULCEROSA AND CROHN'S DISEASE BY ORAL ADMINISTRATION

[75] Inventor: Søren Halskov, Helsinge, Denmark

[73] Assignee: Farmaceutisk Laboratorium Ferring A/S, Vanløse, Denmark

[21] Appl. No.: 555,533

[22] Filed: Nov. 28, 1983

Related U.S. Application Data

[63] Continuation of Ser. No. 270,517, May 29, 1981, abandoned.

[30] Foreign Application Priority Data

Mar. 20, 1980 [DK] Denmark .............................. 1202/80

[51] Int. Cl.$^3$ ......................... A61K 9/22; A61K 9/36; A61K 31/60
[52] U.S. Cl. ................................................... 514/166
[58] Field of Search ......................................... 424/230

[56] References Cited

U.S. PATENT DOCUMENTS 4,190,716  2/1980  Parkinson et al. ..................... 424/78
4,211,777  7/1980  Chambers ............................ 424/232
4,298,595  11/1981  Parkinson et al. .................... 424/78

OTHER PUBLICATIONS

Rasmussen et al., "Treatment of Crohn's Disease with Peroral 5-Aminosalicyclic Acid", *Gastroenterology*, 1983; 85:1350-1353.
Heatley et al., "Disodium Cromoglycate in the Treatment of Chromic Proctitis", Gut, 1975, 16, 559-563.
Mani et al., "Treatment of Ulcerative Colitis with Oral Disodium Cromoglycate", *The Lancet*, Feb. 28, 1976, pp. 439-441.
Dronfield et al., "Comparative Trial of Sulphasalazine and Oral Sodium Cromoglycate in the Maintenance of Remission in Ulcerative Colitis", *Gut*, 1978, 19, 1136-1139.
Buckell, "Controlled Trial of Disodium Cromoglycate in Chronic Persistent Ulcerative Colitis", *Gut*, 1978, 19, 1140-1143.
Willoughby et al., "Comparison of Disodium Cromoglycate and Sulphasalazine as Maintenance Therapy for Ulcerative Colitis", *The Lancet*, Jan. 20, 1979, pp. 119-122.
Pieniaszek, Jr. et al., Journal of Pharmaceutical Sciences, vol. 68, No. 10, Oct. 1979, pp. 1323-1325.
Goodman et al., "Ulcerative Colitis", Clinical Gastroenterology, 1978, pp. 3-16, 25, 73-74, 109-124, 128.
Kirsner, *Jama*, Feb. 8, 1980, vol. 243, No. 6.
Khan et al., "An Experiment to Determine the Active Therapeutic Moiety of Sulphasalazine", *Lancet*, 2, 1977, pp. 892-895.
Peppercorn et al., Gastroenterology 64, 1973, pp. 240-245.
Willoughby et al., Scand. J. Gastroent., 1980, 15, pp. 715-719.
Fischer et al., J. Chromatography, 162 (1979), pp. 237-243.
van Hees et al., *Lancet*, 1, 1978, p. 277.
van Hees et al., Gut, 1979, 20, pp. 300-304.
Schroeder et al., Clin. Pharm. and Ther., vol. 13, No. 4, 1972.
Klotz et al., New Engl. J. of Med., 303, No. 26, Dec. 1980.
Binder et al., "Disodium Cromoglycate in the Treatment of Ulcerative Colitis and Crohn's Disease", Gut, vol. 22, pp. 55-60, 1981.
Shafii et al., "Absorption, Enterohepatic Circulation, and Excretion of 5-Aminosalicyclic Acid in Rates, Gastroenterology, vol. 77, No. 5, 1982 pp. 297-299.

*Primary Examiner*—Shep K. Rose
*Attorney, Agent, or Firm*—Fleit, Jacobson, Cohn & Price

[57] ABSTRACT

A pharmaceutical composition containing as active ingredient 5-aminosalicyclic acid or a pharmaceutically acceptable salt or ester thereof allow the treatment of colitis ulcerosa or Crohn's disease by oral administration. A particular slow-release tablet formation and its preparation is disclosed.

2 Claims, 6 Drawing Figures

FIG. 4

ILEOSTOMY STUDIES - 5-AcASA IN PLASMA
MEAN VALUES, N=6

FIG. 5

PHARMACEUTICAL COMPOSITION AND METHOD FOR THE TREATMENT OF COLITIS ULCEROSA AND CROHN'S DISEASE BY ORAL ADMINISTRATION

This is a continuation of application Ser. No. 270,517, filed May 29, 1981, now abandoned.

The present invention relates to a pharmaceutical composition useful for the treatment of colitis ulcerosa and Crohn's disease, currently denominated "inflammatory bowel diseases" (IBD). The invention also relates to a method for the treatment of IBD.

Colitis ulcerosa is a chronic inflammatory disease of the colon of unknown etiology. In its acute stages it resembles an infectious disease, but no microorganism has been definitively established as its cause. The disease causes inflammations of the mucosa of the colon, with extension to the submucosa in severe cases. Typically, not only the colon, but also the rectum is attacked, but only rarely is the ileum involved. The ulcer formation and its extent vary with the developmental stage of the disease, but can often be detected macroscopically (sigmoidoscopy and colonoscopy). For an exhaustive discussion of the disease and the various surgical and medical methods of treatment reference is made to "Ulcerative colitis", Coodman & Sparberg, Wiley, N.Y. 1978.

The related disease, Crohn's disease, also known as regional enteritis or colitis granulomatosa, which is also discussed by Goodman & Sparberg, is most frequently located in the small intestine (small bowel), especially in the ileum, but may also affect the jejunum and any part of the colon, including the rectum. In the latter case the differentiation of Crohn's disease from ulcerative colitis give rise to great diagnostic problems. Generally, the inflammatory reactions differ from that of colitis ulcerosa by progressing to layers deeper than the mucosa and affecting the epithelium in a lesser degree.

A thorough review of the state of the art with regard to both diseases are given by J. B. Kirsner, JAMA, Feb. 8, 1980, vol. 243, No. 6.

Both diseases have become increasingly frequent especially in the developed countries, and it is estimated that the number of IBD patients in the United States alone exceed 500,000 people, and that the figures continue to increase (Goodman & Sparberg). Therefore, treatment of IBD has become one of the most important problems of modern medicine.

The medical treatment will be further expounded below, but it should briefly be mentioned that failure to respond to medical treatment invariably necessitates surgery, where the standard surgical operation in the treatment of ulcerative colitis is total proctocolectomy (removal of the colon and rectum) with a permanent ileostomy. According to Kirsner, op. cit. 15 to 20% of the patients with colitis ulcerosa require surgical intervention, while the figure in case of Crohn's disease is as high as 40 or 50%.

It is therefore evident that any improvement in the effect of the medical treatment would offer considerable advantages.

Common drugs for medical treatment of colitis ulcerosa and Crohn's disease are corticosteriods, e.g. prednisone, prednisolone and hydrocortisone. A drug recently proposed is 6α-fluoro-11β-hydroxy-3,20-dioxa-16α-methyl-1,4-pregnadiene-21-carboxylic acid butyl ester, cf. PCT Application No. WO 80/00122.

Another drug which has been used for years, especially in the treatment of colitis ulcerosa, is sulfazalazine (salicylazosulfapyridine, SASP) consisting of sulfapyridine (SP) and 5-aminosalicylic acid (5-ASA) coupled via an azo-bond. The mode of action of SASP is unknown (Azad Khan et al., Lancet, 2, 1977, p. 892–895), but it has been shown that when sulfazalazine is taken by mouth, the ordinary mode of administration, it reaches the colon intact where it is split by bacteria into SP and 5-ASA, cf. the following reaction scheme:

So far it has chiefly been assumed that the effect of the drug was primarily due to a topical action on the ulcer sites, Peppercorn and Goldman, Gastroenterology 64, 1973, p. 240–245, but there is still no consensus among researchers whether the effect should be ascribed to the coupling product SASP or one or both of the moieties SP and 5-ASA. One of the difficulties is the limited clinical examination material so that the statistical reliability of the reported results is open to discussion.

An important contribution to the knowledge in this field was made by Azad Khan et al., op. cit., who compared SASP, SP and 5-ASA administered rectally and concluded that the therapeutically active moiety was 5-ASA and that SP only acts as a "carrier" to ensure that 5-ASA is not released until it has reached the colon. Azad Khan chose rectal administration and not oral administration, which is the ordinary mode for SASP, because previous studies of absorption in healthy patients had shown that free 5-ASA is absorbed from the small bowel in particular the jejunum, which was considered inappropriate as it prevented topical action in the colon.

This same point of view is held by Willoughby et al., Scand. J. Gastroent. 1980, 15, 715–719, who undertook enema studies on the derivative N-acetyl-5-aminosalicylic acid (5-AcASA). They concluded that 5-AcASA resembled 5-ASA in its effect on the inflamed mucosa in ulcerative colitis, but that neither were suitable as oral agent. Instead they suggested further studies into substituted salicylates.

Consistently therewith J. B. Kirsner, op. cit., in his review article concludes that therapeutic hopes for the future amongst other things include the combination of 5-ASA with a carrier molecule that is less toxic than sulfapyridine.

The work of Azad Khan et al., which has been confirmed by van Hees et al., Lancet, 1, 1978, p. 277, has not carried enough conviction to prevent Fischer and Klotz, J. Chromatography, 162 (1979), p. 237–243 from stating that till now SP has been considered the biologically active moiety of SASP, but that said two works have shown that 5-ASA also has therapeutic effect, so plasma concentration measurements of 5-ASA and its major metabolite 5-acetylaminosalicylic acid (5-AcASA) might be of some help in increasing the therapeutic efficacy of SASP and evaluating its mechanism of activity.

It should be mentioned that while it has been demonstrated that SP is highly absorbed from the colon and then metabolized by acetylation and glucuronidation in the liver before it is excreted in the urine, the major part of the released 5-ASA is not absorbed but excreted in the feces, partly as 5-ASA and partly as 5-AcASA (Peppercorn & Goldman, op. cit., Azad Khan, op. cit., and van Hees et al., Gut, 1979, 20, p. 300–304), a minor portion being excreted in the urine in the form of the metabolite 5-AcASA. The amount excreted in the urine varies from about 15% to 35% in said articles, where in several cases only healthy patients have been examined since the primary object was to study the mechanisms of absorption. However, it must be assumed that precisely the huge difference in absorption of SP and 5-ASA is one of the reasons why several researchers still believe that SP has its share of the responsibility for the effects of SASP.

Though Azad Khan thus found that 5-ASA when administered rectally exhibits a useful therapeutic activity like SASP, he excludes oral administration, and having observed a considerable instability of 5-ASA in aqueous suspension he proposes to synthetize a new compound without these drawbacks. The disadvantages of SASP as such include a plurality of side effects, such as nausea and vomitting, skin rashes, anemia, arthralgias, headache, etc., cf. Goodman and Sparberg, op. cit. which in case of severe attacks of colitis ulcerosa have inhibited the use of desirably high doses, which has made it necessary to combine the treatment with administration of corticosteriods with their well-known drawbacks. Another serious disadvantage is that a considerable amount of the patients (up to 10%) are allergic to sulfa drugs, thereby excluding SASP treatment.

Conclusively, it might therefore be said that experts agree in the desirability of providing a drug with improved activity over SASP, and in the possibility of achieving such improvement with 5-ASA as starting point. However, opinions are divided as to the significance of 5-ASA, and it is considered inappropriate to use this compound because of its instability and because it is absorbed before it reaches the colon if it is administered orally. If, however, the problems of stability could be solved it should be possible to use the compound in rectal drugs.

The object of the present invention is to provide an improved pharmaceutical composition useful for the treatment of colitis ulcerosa or Crohn's disease by oral administration and a method for such treatment.

The invention is based on the fact that the rooted prejudice against oral administration of 5-ASA as free acid has surprisingly been overcome because in this mode, too, 5-ASA and its salts and esters have a useful therapeutic effect on colitis ulcerosa, in particular when administered in the form of sustained-release tablets.

Accordingly the invention relates to a pharmaceutical composition useful for the treatment of Colitis ulcerosa or Crohn's disease by oral administration, which comprises as essential active ingredient an effective amount of 5-aminosalicylic acid or a pharmaceutically acceptable salt or ester thereof in admixture with a pharmaceutically acceptable carrier. The salts of 5-ASA may be acid addition salts, in particular the hydrochloride, but any pharmaceutically acceptable, non-toxic organic or inorganic acid may be used.

Also salts formed with the carboxylic acid group may be used. As examples may be mentioned alkali metal salts (K, Na), alkaline earth metal salts (Ca, Mg), but again any pharmaceutically acceptable, non-toxic salt may be used. The Na- and Ca-salts are preferred.

In Danish patent appln. No. 1270/77, available to public inspection and being incorporated herein by reference, a number of esters of ortho-, meta- and para-salicylic acid are disclosed. Said esters are effective as ultraviolet ray screening compounds thereby rendering themselves useful in preventing solar burning. The disclosed meta- (or 5-) aminosalicylic esters and a number of related esters are also applicable in the composition according to the invention.

Applicable esters are e.g.

straight chain or branched $C_1$–$C_{18}$ alkyl esters, e.g. methyl, ethyl, propyl, isopropyl, butyl, isobutyl, amyl, hexyl, heptyl, octyl, nonyl, decyl, lauryl, myristyl, cetyl, and stearyl, etc., straight chain or branched $C_2$–$C_{18}$ alkenyl esters, e.g. vinyl, allyl, undecenyl, oleyl, linolenyl, etc., $C_3$–$C_8$ cycloalkyl esters, e.g. cyclopropyl, cyclobutyl, cyclopentyl, cyclohexyl, cycloheptyl and cyclooctyl, etc., aryl esters, e.g. phenyl, toluyl, xylyl, naphthyl, etc., alicyclic esters, e.g. menthyl, etc., or aralkyl esters, e.g. benzyl, phenethyl, etc.

Generally speaking the proper selection of the active ingredient depends on the selected type of formulation, the disease pattern, especially the site and type of the disease, and the desired release of the active ingredient, as shall be further expounded below together with the concept "effective amount".

The physical state and solubility characteristics of the 5-ASA derivatives must be taken into account when selecting a suitable carrier composition for the ingredient.

The preferred active ingredient at present is the free acid, 5-aminosalicylic acid.

In the previous oral administrations of 5-ASA only the mechanism of absorption was examined, and it was concluded that the compound is essentially completely absorbed from the small bowel, as no noticeable amounts of 5-ASA or 5-AcASA were observed in the feces. The studies were exclusively made in animals (rats), cf. Peppercorn and Goldman, Gastroenterology 64, 1973, p. 240–45, or in healthy volunteers (Schröder and Campbell, Clin. Pharm. and Ther. vol. 13, No. 4, 1972). The effect of SASP was, as mentioned, believed to be caused by topical action (Peppercorn et al., op. cit.) and accordingly no material on a possible effect of 5-ASA per os is available.

Without tying it down to any specific theory, it is believed that owning to three reactive groups —COOH, —OH and —NH$_2$, 5-ASA establishes hydrogen bonds to the linear proteins in connective tissues, i.a. in the colon, and thereby exerts a kind of a "depot effect" on colitis ulcerosa. This seems to be in good harmony with Fischer and Klotz, J. Chromatography 162 (1979) p. 237–243, who demonstrated very low serum concentrations of 5-ASA and its metabolization product 5-AcASA by plasma concentration measurements after oral administration of 4 g of SASP.

A particularly interesting aspect of the invention is the use of the composition in the treatment of Crohn's disease. In this respect SASP has not proved to be very effective, at least not in the most frequent case, where the disease is limited to the ileum. Reference is made to Peppercorn and Goldman, op. cit. p. 244, van Hees et al., Gut 1979, op. cit. p. 300, Kirsner, op. cit., p. 559 and Klotz et al., New Engl. J. of Med. 303, No. 26, dec. 1980. This is probably due to the above-mentioned fact that SASP is not split under release of 5-ASA until it reaches the colon. In the less frequent case, where Crohn's disease also extends to or is limited to the colon and rectum, SASP has proved effective, but of course accompanied by its well-known side effects.

As shown below in clinical tests on ileostomy patients up to 50% of the 5-ASA administered in the form of a composition according to the invention may be absorbed from the small bowel thereby rendering an effect on Crohn's disease highly probable.

In addition to the obvious advantages for the patients offered by oral administration rather than rectal, e.g. by way of retention enemas, oral administration of 5-ASA has a significantly advantage in terms of effect. For van Hees et al., Gut, 1979, 20, 300–304 (op. cit.) has demonstrated that the absorption of 5-ASA from the colon following administration of SASP is drastically decreased in case of diarrhoea which frequently accompanies colitis ulcerosa, in particular in severe cases.

The effective oral dose depends on the extent of the disease and for adults it usually amounts to 0.5 to 1.0 g twice a day. Generally about 20 mg/kg body weight of 5-ASA or a salt or ester thereof (calculated as 5-ASA) will be the recommended initial daily dosage subject to adjustment in accordance with the observed results of the treatment. In particular the dosage for children should be adjusted by means of serum concentration measurements.

5-ASA and its derivatives can be formulated as ordinary oral drugs such as tablets or capsules by admixture with suitable pharmaceutical carriers which are well-known to the artisan, e.g. lactose, maize starch, potato starch, and lubricants, e.g. magnesium stearate and talc. A preferred carrier constituent is a microcrystalline cellulose having approximately the same density as 5-ASA thereby preventing sedimentation and resulting heterogenicity during tablet production. Generally, tablets in the form of slow-release tablets are preferred, but also enterosoluble tablets may be used.

A particularly advantageous slow-release tablet has been developed the preparation of which is illustrated in the following non-limiting example, based on the production of 1000 tablets containing 250 mg of the active ingredient. (All ingredients pharmaceutical grade).

EXAMPLE

Preparation of granulate I 250 g of 5-ASA are granulated to a particle size of from 0.7–1 mm with 25 g of polyvinylpyrrolidone dissolved in isopropanol (1:9 w/w). Upon evaporation of the isopropanol the resulting dry granulate is sprayed with 45 g of ethyl cellulose dissolved in acetone (3:97 w/w) resulting in granulate particles individually coated with ethyl cellulose upon evaporation of the acetone.

Preparation of granulate II 270 g of microcrystalline cellulose and 60 g of potato starch are granulated with about 33 g of the above polyvinylpyrrolidone solution to the same particle size.

The resulting about 320 g of the coated granulate I are mixed with a lubricant mixture of 3 g of sodium stearate and 27 g of talc and with dry granulate II to form 650 g of total granulate which are pressed to form tablets with a diameter of 13.5 mm and a weight of 650 mg/tablet containing 250 mg of 5-ASA.

The resulting tablets were used in the clinical tests described below. As shown in the tests with ileostomy patients about 50% of the active ingredient is released in the small bowel, the remainder being available to the colon. By controlling the release a preparation with predominant effect versus Crohn's disease or colitis ulcerosa according to the site of the disease of the individual patient can be obtained. The above formulation is believed to represent an effective compromise applicable versus both diseases.

Generally the release can be controlled by variating one or more of the following:
(a) The particle size of the granulated active ingredient.
(b) The thickness and permeability (swelling properties) of the coating.
(c) The active ingredient proper.
(d) The pH-conditions within the coated particle.

Thus in case of Crohn's disease, where an early release of the active ingredient in the small bowel is desirable, one may select a relatively small particle size, e.g. about 0.7 mm or less and a relatively thin coating, e.g. by lowering the ethyl cellulose amount used or select a more permeable coating material, and an active ingredient with a good solubility at pH 7.5 which is the prevailing pH in the small bowel.

In case of colitis ulcerosa, where a delayed release of the active ingredient until the colon is reached is desirable, one may select an active ingredient having a good solubility at pH 6 which is the prevailing pH in the colon and a greater particle size, e.g. about 1 mm or more, and a relatively thick coating.

The most effective composition of the tablet taking the individual patient's disease pattern into account can be found by routine tests once the pharmaco-kinetic relationships are more clearly established.

In particular the solubility, acidity, and susceptibility to hydrolysis of the different derivatives of 5-ASA, such as acid addition salts, salts formed with the carboxylic group, e.g. alkali metal salts, alkaline earth metal salts, etc., and esters, e.g. alkyl, alkenyl, aryl, aralkyl, cycloalkyl esters, etc., under different pH conditions may be used as guidelines for the proper choice. Also suitable pH-conditions might be established within the coated particles by adding to granulate I besides the active ingredient a suitable buffer in accordance with the desired release pattern.

The invention also relates to a method for the preparation of a sustained release tablet as defined in claim 9.

Besides the above-mentioned variations in order to obtain the desired release the tablet ingredients may also be variated. While the preferred organic solvent for the polyvinylpyrrolidone is isopropanol, other organic solvents may also be used, as long as they do not in a significant degree act as solvents for the selected 5-ASA derivative.

While the preferred coating agent is ethyl cellulose other coating agents may also be used, provided they secure the desired release pattern. In particular a number of other cellulose derivatives must be assumed to be applicable.

Depending on the selected active ingredient one may also depart from the proportions laid down in claim 9 and the example. In particular one may leave out Granulate II or substitute for Granulate II a conventional pharmaceutical tablet carrier, provided that the active ingredient has the necessary stability.

Clinical test results

Before subjecting 5-ASA to clinical tests animal studies were carried out.

Toxicity test

The acute toxicity in rats and mice was examined in accordance with the directions of Ph. Nord.

No toxic reactions were observed when 5-ASA was administered intravenously in doses op up 500 mg/kg in mice and up to 200 mg/kg in rats.

It is the purpose of the clinical studies described below to estimate the bioavailability of a sustained-release type 5-ASA table (Pentasa®) of the composition described above in the example by the study of 5-ASA/5-AcASA plasma levels in healthy volunteers as well as the excretion pattern in urine and feces.

Furthermore the availability of 5-ASA for the small bowel alone was investigated in the ileostomy effluents of a group of patients.

METHODS AND MATERIALS

5-ASA tablet

A sustained-release type tablet containing 250 mg of 5-ASA (Pentasa®). Only trace amounts of 5-ASA are released in the stomach at normal gastric pH. At pH 7.5 as is usual in the jejunum 5-ASA was released linearly in relation to time, all 5-ASA being released in 12 hours. At pH 6, the usaul acidity of the colon, the release of 6-ASA from the tablet, was reduced. This unforeseeable and surprising release pattern should in principle ensure a continuous release of 5-ASA through the whole length of colon.

Determination of 5-ASA and 5-AcASA in biological fluids

Procedures for the determination of 5-ASA and 5-AcASA in ileostomy effluents, feces, urine and blood were based on a newly developed HPLC assay combined with fluorescens spectophotometry. The detection limit of the procedure was found to be less than 0.03 mg of 5-ASA/ml in biological fluids.

SUBJECTS STUDIED

Ileostomy patients

Six ileostomy patients colectomized because of colitis ulcerosa with intact small bowel were studied. Their distribution as to sex, age, height, body weight, time since colectomy, small bowel transit time (carmine), and acetylator phenotype (v. Fischer and Klotz, op. cit.) (assessed by sulphadimidine) are shown below in table I.

Healthy volunteers

Fourteen healthy persons consented to volunteer. They had no previous or present symptoms or signs of gastrointestinal or other disease apart from uncomplicated appendectomy. There were seven females and seven males. Mean age and age range were for the women 32.4 years and 29–37 years, and for the males 32 years and 24–40 years, respectively. Mean body weight and weight range were for the females 58.6 kg and 53–67 kg, and for the males 70.9 kg and 60–83 kg, respectively. There were eight slow and 6 fast acetylators. Their biographical data are shown in table II below.

STUDY PLAN

Ileostomy patients

Figure 2:
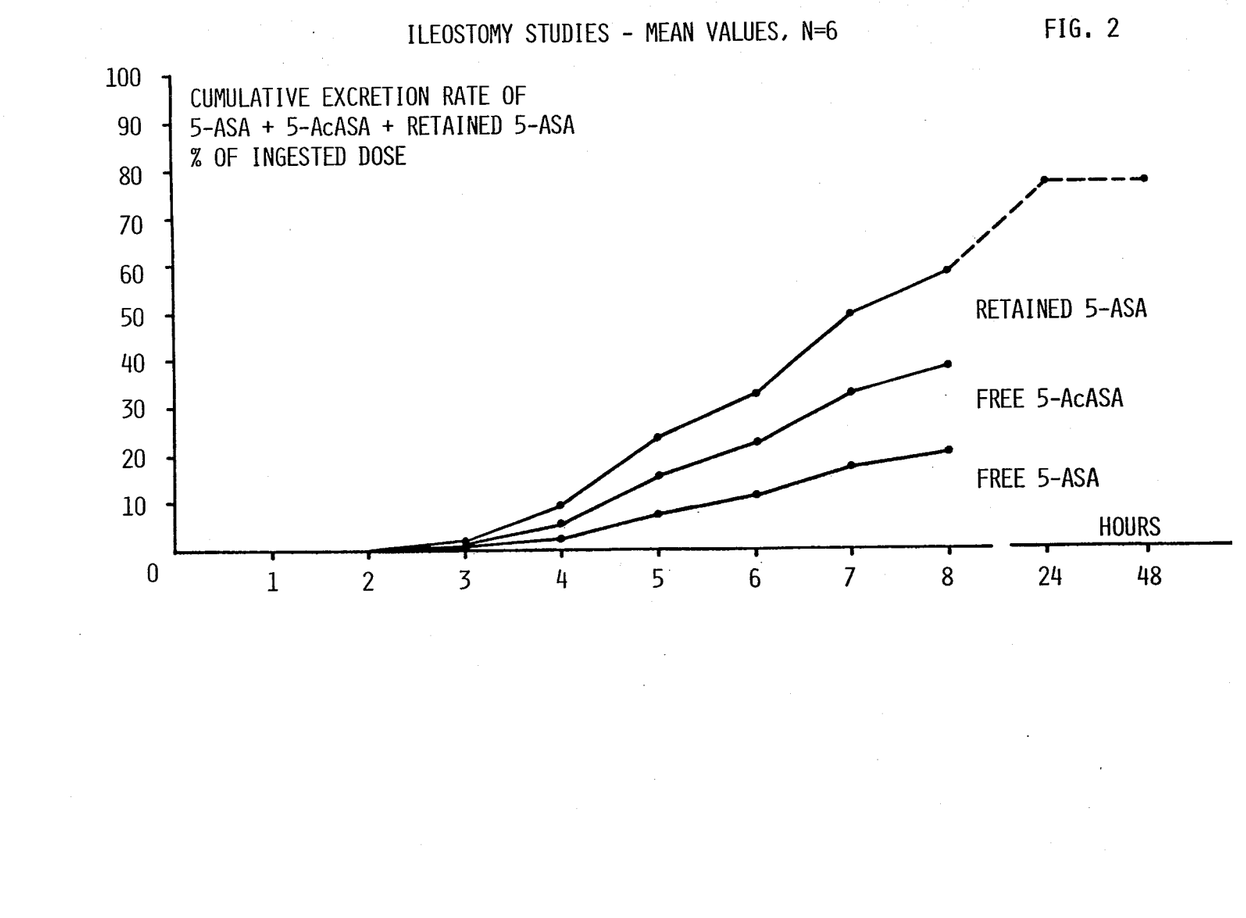
Figure 3:
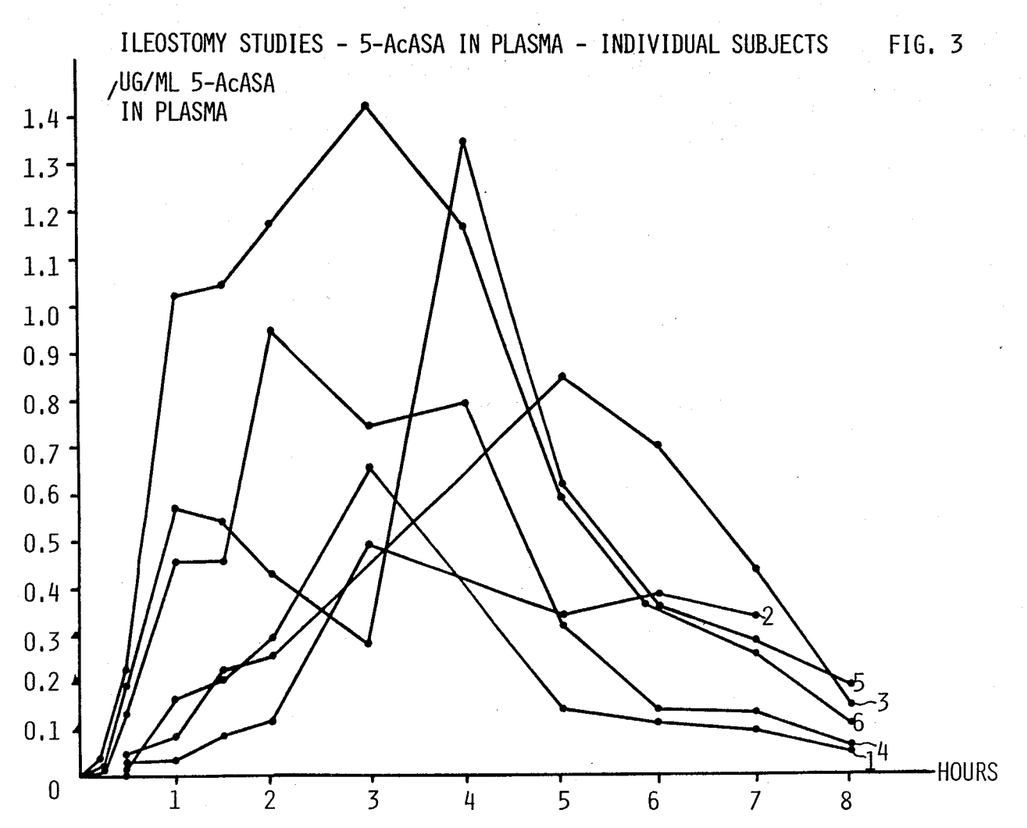
Figure 4:
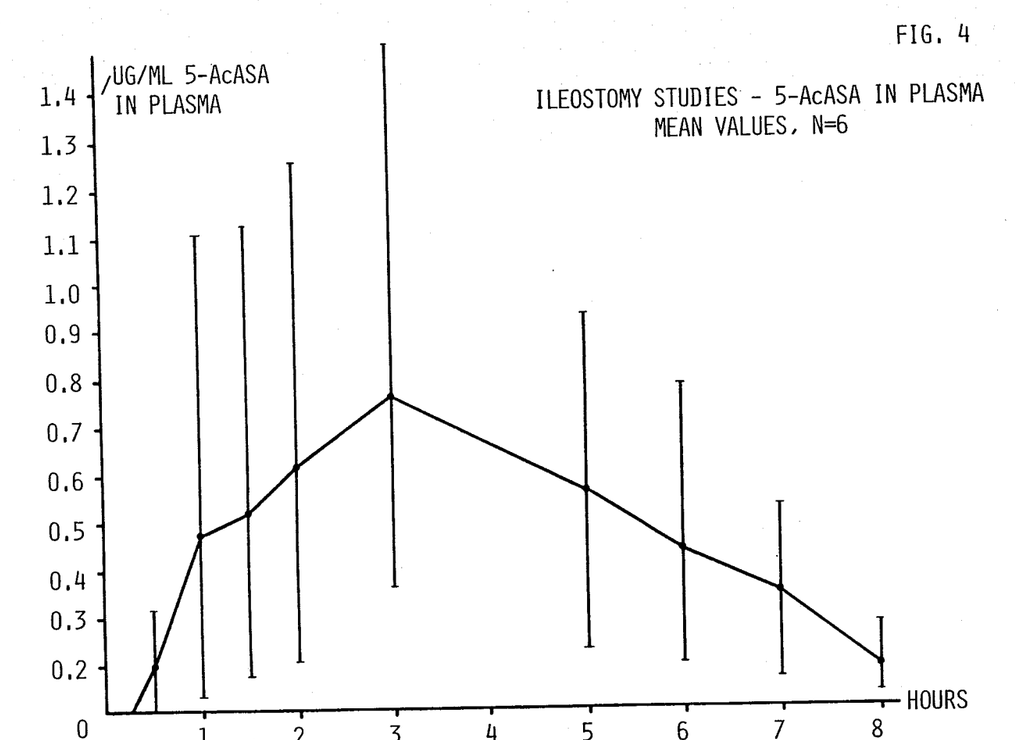

A single dose of two tablets of sustained-release 5-ASA, i.e. total dose 500 mg, were ingested at 8 a.m. by the fasting patient who thereafter took a normal continental breakfast, lunch at noon, and dinner at 6 p.m. Ileostomy effluents were collected every hour for eight hours (FIGS. 1 and 2) urine was collected over an 8 hour period and venous blood was drawn at intervals through the first eight hours (FIGS. 3 and 4).

Volunteers

Each subject took two 5-ASA tablets, i.e. 500 mg 5-ASA, three times a day for six days, at 8 a.m., 4 p.m. and at midnight expt for the first day, where the two first ingestions took place at 9 a.m. and 5 p.m. The injections are shown by arrows on FIGS. 5 and 6.

Figure 5:
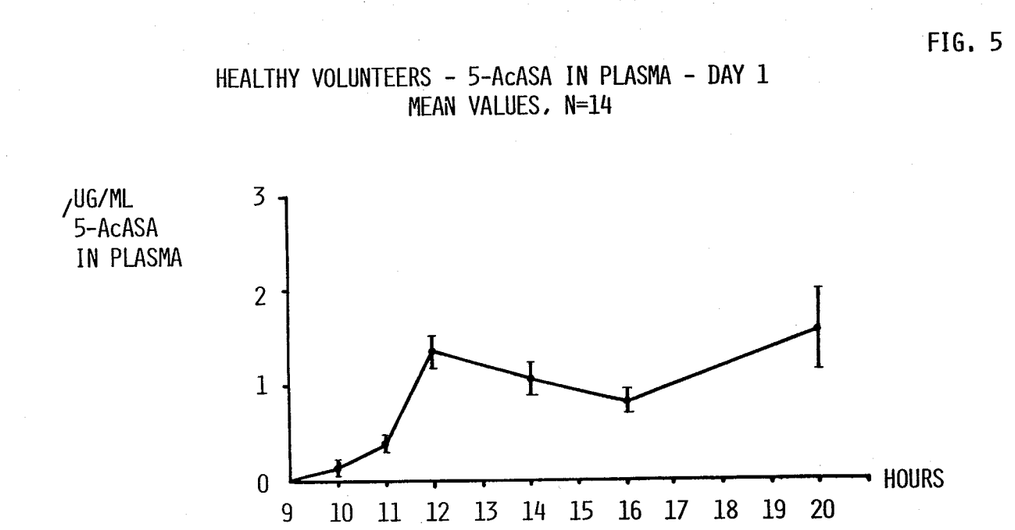
Figure 6:
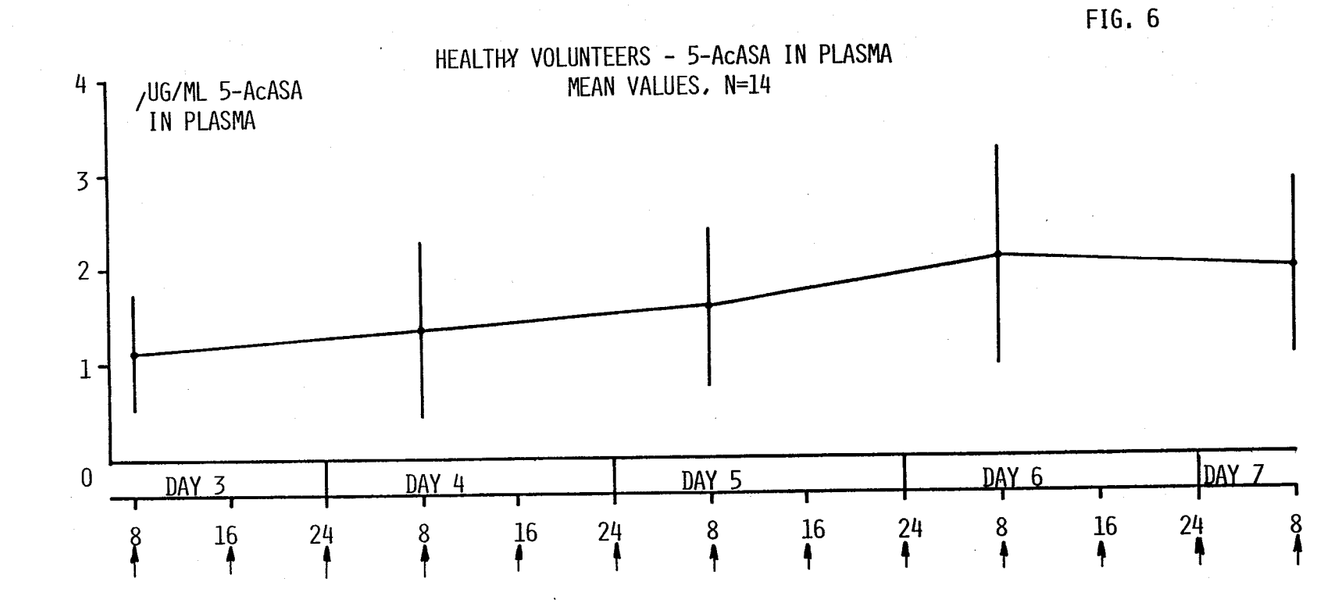

The two tablets at 8 a.m. were taken by the fasting subject. Venous blood samples for determination of 5-ASA and 5-AcASA were drawn at intervals throughout the first day (FIG. 5) and at 7.50 the following five days (i.e. before the 8 a.m. tablets were ingested) (FIG. 6). Twenty-four hour urine and faecal samples were collected on the 6th day for quantitative determination of 5-ASA and 5-AcASA. Every day throughout the study period of six days a single faecal sample was analyzed qualitatively for the presence of 5-ASA and 5-AcASA.

SAFETY MONITORING

In both parts of the study, ileostomy patients as well as the healthy volunteers filled in diary sheets concerning specified signs and symptoms (nausea, vomiting, headache, dizziness, visual and auditory sensations, abdominal pain or discomfort, constipation, diarrhoea, muscle-joint sensations and skin manifestations). Blood pressure and pulse rate were monitored and on—as well as off—study analysis of hemoglobin, reticulocytes, thrombocytes, leucocytes, coagulation factors, S-alamine-amino-transferases, Se-urea, S-Creatinin together with urine analysis for albumin, glucose and sediment were carried out.

ETHICS

All participants in the study were informed about the background, goals and procedures by oral and written instructions. Informed consent by signature was obtained in all cases.

TABLE I

| | | | | Biographical data for the six ileostomy patients | | | |
|---|---|---|---|---|---|---|---|
| No. | Sex | Age years | Ileostomy age years | Height cm | Body weight kg | Small bowel transit time hours | Acetylator phenotype |
| 1 | f | 47 | 4½ | 166 | 70 | 4¼ | slow (0.33) |
| 2 | f | 47 | 3 | 169 | 60 | 2¾ | slow (0.24) |
| 3 | m | 19 | ½ | 182 | 83 | 5½ | slow (0.27) |

TABLE I-continued

| | | | Biographical data for the six ileostomy patients | | | | |
|---|---|---|---|---|---|---|---|
| No. | Sex | Age years | Ileostomy age years | Height cm | Body weight kg | Small bowel transit time hours | Acetylator phenotype |
| 4 | m | 23 | 5 | 190 | 81 | 4½ | slow (0.33) |
| 5 | m | 23 | 2 | 178 | 80 | 4¾ | fast (0.81) |
| 6 | f | 21 | 1½ | 167 | 57 | 3½ | slow (0.26) |
| N = 6 | 3 f | | | | | | 5 slow |
| | 3 m | | | | | | 1 fast |
| Mean | f | 22.7 | 3.0 | 167 | 62.3 | 3¼ | |
| Mean | m | 21.7 | 2½ | 183 | 81.3 | 5 | |
| Mean total | | 22.2 | 2¾ | 175 | 71.8 | 4¼ | |

TABLE II

| | | Biographical data for healthy human volunteers | | | |
|---|---|---|---|---|---|
| No. | Sex | Age years | Height cm | Body weight kg | Acetylator phenotype |
| 1 | m | 33 | 185 | 78 | slow (0.30) |
| 2 | f | 34 | 158 | 54 | slow (0.25) |
| 3 | m | 31 | 178 | 64 | fast (0.76) |
| 4 | f | 29 | 169 | 57 | slow (0.21) |
| 5 | m | 35 | 182 | 83 | slow (0.24) |
| 6 | f | 32 | 167 | 53 | slow (0.32) |
| 7 | m | 27 | 182 | 75 | slow (0.22) |
| 8 | f | 30 | 176 | 67 | fast (0.70) |
| 9 | m | 24 | 178 | 65 | fast (0.73) |
| 10 | f | 30 | 160 | 56 | fast (0.85) |
| 11 | m | 40 | 178 | 71 | fast (0.71) |
| 12 | f | 35 | 168 | 58 | slow (0.23) |
| 13 | m | 34 | 182 | 60 | slow (0.33) |
| 14 | f | 37 | 169 | 65 | fast (0.66) |
| 7 m | | | | | slow 8 |
| 7 f | | | | | fast 6 |
| Mean | f | 32.4 | 166.7 | 58.6 | |
| Mean | m | 32.0 | 180.7 | 70.9 | |
| Mean total | | 32.2 | 173.7 | 64.7 | |

RESULTS

Ileostomy patients

Figure 1:
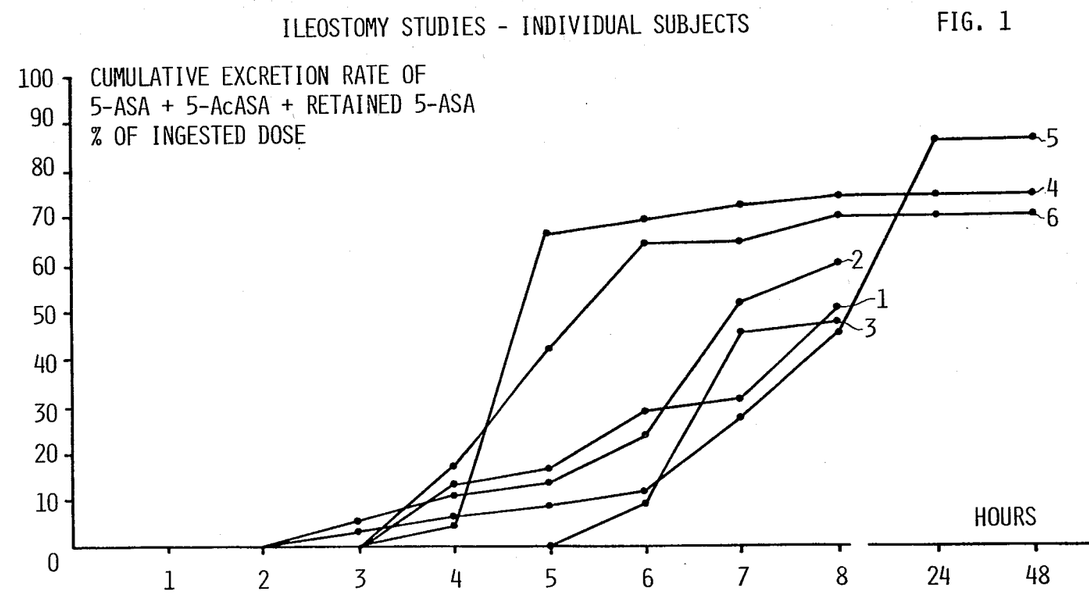

A cumulative excretion rate of 5-ASA and 5-AcASA via ileostomy effluents from the individual subjects is shown in FIG. 1. FIG. 2 illustrates the ratios between free 5-ASA and 5-AcASA in the ileostomy secretions and 5-ASA still retained in the granules of the sustained-release preparation based on the mean values from FIG. 1. From the figures is seen that no 5-ASA or 5-AcASA could be detected in ileostomy secretions during the first two hours. During the following hours free 5-ASA and 5-AcASA were registered in the effluents as they were excreted at constant rates up to 8 hours after ingestion of the tablets. At that time 58% of the ingested total dose was collected in the ileostomy bags. This portion was equally distributed among three parts: one third as free 5-ASA, another third as free 5-AcASA and the last third as 5-ASA still retained in the granules. However, in three of the subjects the collecting time was expanded further up to 48 hours after ingestion (see FIG. 1). In one of these a further 20% 5-ASA was found indicating that more than one third of the 5-ASA was retained in the granules in this patient.

In the blood plasma the concentrations measured during the study are shown in FIG. 3 (individual values) and FIG. 4 (mean values. Bars indicate total ranges). Before ingestion of 5-ASA plasma concentrations were zero in all six cases. Trace amounts of 5-AcASA were found half an hour after ingestions. Peak concentrations of 5-AcASA amounted to 0.5–1.4 $\mu$g/ml within an interval of 2–5 hours after ingestion of 5-ASA. In the urine collected no 5-ASA was found except in one case where 1.4 mg 5-ASA was found. Within 8 hours after ingestion of 5-ASA a mean of 60 mg 5-AcASA was found, ranging from 42–82 mg. This corresponds to a means of 12% and a range from 8–16% of the ingested dose, respectively.

No signs or symptoms and no change in results of biochemical examination of blood or urinary control parameters indicated any untoward symptomatic or toxic effect of the ingested drug.

Normal healthy volunteers

As was found in the series of ileostomy patients, in this part of the study where fourteen subjects took sustained-release 5-ASA (Pentasa ®) 500 mg t.i.d. for six days, no 5-ASA or 5-AcASA was detected the morning of day one before ingestion of 5-ASA. Similarly, during the whole study, only 5-AcASA was detected in plasma and urine. Variations of plasma concentrations of 5-AcASA are shown in FIGS. 5 and 6. The indicated values represent mean values of 14 observations ±2 SEM (95% confidence limit). After ingestion of the first dose of 500 mg 5-ASA on day one a rise in plasma concentration of 5-AcASA similar to the values found in the ileostomy patients is observed, rising to a mean value of 1.3 $\mu$g/ml—Thereafter a fall is registered and then following ingestion of a second dose of 5-ASA another rise up to a little higher values, resulting in a mean value of 1.6 $\mu$g/ml three hours after ingestion of the second dose (see FIG. 5). During the following days up to day 5 the mean values are slowly increasing up to a level of about 1.8 $\mu$g/ml, as seen from FIG. 6. This level, corresponding to a 95% confidence interval of the mean from 1.7 to 2.2 $\mu$g/ml is maintained day 6 indicating that steady state levels are reached. The total range of 5-AcASA plasma concentrations in all fourteen subjects on day six was from 1.20—2.83 $\mu$g/ml.

Urinary excretions of free 5-ASA could not be recorded. On day 6, in steady state, a mean of 737 mg 5-AcASA was excreted during 24 h (calculated as 5-ASA). The excretions ranged from 447 to 1304 mg per 24 h. The 95% confidence limits of the mean value of 5-AcASA excretions were 587–887 mg per 24 h.

In faeces a daily qualitative analysis showed presence of 5-ASA and 5-AcASA in morning samples from day 2 throughout the study. Quantitative analysis on day 6, in steady state, showed a total mean faecal excretion of free 5-ASA and 5-AcASA of 514 mg per 24 h, a range from 84 to 877 mg and 95% confidence limits of the mean excretion of 378–650 mg per 24 h.

Thus in steady state condition on day 6 the mean recovery rate (daily ingested total dose 1500 mg 5-ASA) was 83%.

Also an analysis was made in an attempt to establish the faecal content of granules. However, the analysis was not carried out until 24 hours after the collection of the faeces, which means that some of the granules have released their content of 5-ASA. The average total of 5–10% therefore accounts for both released and non-released 5-ASA. The important thing is that in case of patients instead of healthy volunteers the 5-ASA would have been available in the colon.

The tests did not show a significant variation according to differences in acetylator phenotype (slow and fast acetylators) indicating that the acetylation does not only take place in the liver but also in the tissues. No results of analysis of control parameters pointed toward any untoward side effect, this being as to symptoms, signs, biochemical analysis or examinations of urinary sediments. In this part of the study these examinations were repeated at an interval of 1–2 weeks after conclusion of the study.

In conclusion, the above studies seem to indicate that the substained-release 5-ASA (Pentasa®) is a suitable preparation for the treatment of colitis ulcerosa as well as of Crohn's disease, including cases with small bowel affection.

I claim:

1. A method for the treatment of ulcerative colitis or Crohn's disease comprising orally administering an effective amount of a composition consisting essentially of free 5-aminosalicylic acid in admixture with a pharmaceutically acceptable carrier which will control the release of said effective amount of 5-aminosalicylic acid to be administered according to the actual site of said ulcerative colitis or Crohn's disease in an individual patient.

2. A method for the treatment of ulcerative colitis or Crohn's disease comprising orally administering an effective amount of a composition consisting essentially of free 5-aminosalicylic acid in admixture with an orally administrable pharmaceutical carrier which will control the release of said effective amount of 5-aminosalicylic acid to be administered according to the actual site of said ulcerative colitis or Crohn's disease in an individual patient.

* * * * *

UNITED STATES PATENT AND TRADEMARK OFFICE
CERTIFICATE OF CORRECTION

PATENT NO. : 4,496,553
DATED : January 29, 1985
INVENTOR(S) : SØREN HALSKOV

It is certified that error appears in the above-identified patent and that said Letters Patent is hereby corrected as shown below:

On The Title page:

After "[22]," delete "Filed: Nov. 28, 1983" and substitute

--PCT Filed: Mar. 20, 1981--.

After line "[22]" insert the following:

--[86] PCT No.: PCT/DK81/00027

§ 371 Date: May 29, 1981

§ 102(e) Date: May 29, 1981

[87] PCT Pub. No.: WO81/02671

PCT Pub. Date: Oct. 1, 1981--

Signed and Sealed this

Twenty-sixth Day of November 1985

[SEAL]

Attest:

DONALD J. QUIGG

Attesting Officer

Commissioner of Patents and Trademarks

REEXAMINATION CERTIFICATE (881st)
United States Patent [19]
Halskov

[11] B1 4,496,553
[45] Certificate Issued Jun. 28, 1988

[54] PHARMACEUTICAL COMPOSITION AND METHOD FOR THE TREATMENT OF COLITIS ULCEROSA AND CROHN'S DISEASE BY ORAL ADMINISTRATION

[75] Inventor: Søren Halskov, Helsinge, Denmark

[73] Assignee: Farmaceutisk Laboratorium Ferring A/S, Vanløse, Denmark

Reexamination Request:
No. 90/001,176, Feb. 27, 1987

Reexamination Certificate for:
| | |
|---|---|
| Patent No.: | 4,496,553 |
| Issued: | Jan. 29, 1985 |
| Appl. No.: | 555,533 |
| Filed: | Nov. 28, 1983 |

Certificate of Correction issued Nov. 26, 1985.

[63] Continuation of Ser. No. 270,517, May 29, 1981, abandoned.

[30] Foreign Application Priority Data

Mar. 20, 1980 [DK] Denmark ............................. 1202/80

[51] Int. Cl.⁴ ........................... A61K 9/22; A61K 9/52
[52] U.S. Cl. .................................... 424/468; 424/457; 514/159; 514/162; 514/166
[58] Field of Search ...................... 424/78, 79, 81, 457, 424/468; 514/159, 162, 166

[56] References Cited

U.S. PATENT DOCUMENTS

| | | |
|---|---|---|
| 2,805,977 | 9/1957 | Robinson et al. |
| 2,928,770 | 3/1960 | Bardami |
| 2,987,445 | 6/1961 | Levesque |
| 3,039,933 | 6/1962 | Goldream |
| 3,080,294 | 3/1963 | Eberperd |
| 3,081,233 | 3/1963 | Enz et al. |
| 3,108,046 | 10/1963 | Harbit |
| 3,131,123 | 4/1964 | Masquelier |
| 3,133,863 | 5/1964 | Tansey |
| 3,143,472 | 8/1964 | Lappas et al. ............ 424/482 |
| 3,388,041 | 6/1968 | Gaus et al. |
| 3,431,338 | 3/1969 | Munzel ..................... 424/482 |
| 3,784,683 | 1/1974 | Prillig et al. ............ 424/472 |
| 3,906,086 | 9/1975 | Guy et al. |
| 3,950,521 | 4/1976 | Higuchi et al. |
| 4,066,756 | 1/1978 | Orr et al. ................. 424/232 |
| 4,190,716 | 2/1980 | Parkinson et al. ........ 424/78 |
| 4,193,985 | 3/1980 | Bechgaard et al. ....... 424/4 |
| 4,211,777 | 7/1980 | Chambers |
| 4,298,595 | 11/1981 | Parkinson et al. |
| 4,298,595 | 11/1981 | Parkinson et al. ........ 424/78 |
| 4,312,806 | 1/1982 | Lambert et al. .......... 260/149 |
| 4,374,932 | 2/1983 | Pitzele et al. ........... 424/79 |
| 4,440,763 | 4/1984 | Lover ....................... 514/166 |
| 4,455,305 | 6/1984 | Rokos ....................... 514/150 |
| 4,476,553 | 1/1985 | Halskov .................... 514/166 |
| 4,539,198 | 9/1985 | Powell et al. ............ 514/960 |
| 4,540,685 | 9/1985 | Bauer ....................... 514/162 |
| 4,559,330 | 12/1985 | Agback et al. ........... 514/166 |
| 4,591,584 | 5/1986 | Agback ..................... 514/160 |
| 4,632,921 | 12/1986 | Bauer ....................... 514/163 |

FOREIGN PATENT DOCUMENTS

| | | |
|---|---|---|
| 1202/80 | 3/1980 | Denmark . |
| 0040590 | 11/1981 | European Pat. Off. . |
| 0148811 | 7/1985 | European Pat. Off. . |
| WO81/02671 | 10/1981 | PCT Int'l Appl. . |
| WO81/02672 | 10/1981 | PCT Int'l Appl. . |
| WO83/00435 | 2/1983 | PCT Int'l Appl. . |
| 1423985 | 2/1976 | United Kingdom . |
| 2021409A | 12/1979 | United Kingdom . |

OTHER PUBLICATIONS

Goldman, Peter-Declaration.
Pepercorn, March A.-Declaration.
Banker, Gilbert S.-Declaration.
Khan et al, The Lancet, Oct. 29, 1977, 892–896, "An Experiment to Determine . . . Moiety of Sulphasalazine".
Peppercorn et al, Gastroenterology 64:240–245, 1973, vol. 64, No. 2.
Schroder and Campbell, Clinical Pharmacology and Therapeutics, pp. 539–551.
Goldman et al, Gastroenterology 65: 166–169, 1973, vol. 65, No. 1.
Goldman et al, The New England Journal of Medicine, vol. 293, No. 1, pp. 20–23.
Pieniaszek, Jr. et al, Journal of Pharmaceutical Sciences, 1323, vol. 68, No. 10, Oct. 1979.
Klotz et al, Sulfasalazine and its Metabolites, vol. 303, No. 26, pp. 1499–1502, Dec. 25, 1980.
Physician's Desk Reference, p. 1302, copyright 1969.
Physician's Desk Reference, p. 985, copyright 1978.
Pentikainen et al, American Review of Respiratory Disease, vol. 108, 1973.
Wagner et al, American Review of Respiratory Disease, vol. 108, 1973.
J. C. Colbert, Controlled Action Drug Forms, 1974.
Lehman, K., Pharma International, 3, 1–16 (1971).
Schroeter, Louis, Remington's Pharmaceutical Sciences, 1970, 14th Ed., Chapter 88.
Ellis et al, The Theory and Practice of Industrial Pharmacy, 1970, Chapter 10.
Kakemi et al, Chem. Abst., vol. 67, #115435w (1967).
Vavilin et al, Chem. Abst., vol. 77, #49594a (1972).
Wagner et al, Chem. Abst., vol. 79, #45733p (1973).
Badawi et al, Chem. Abst., vol. 94 #127217x (1981).

(List continued on next page)

*Primary Examiner*—Shep K. Rose

[57] ABSTRACT

A pharmaceutical composition containing as active ingredient 5-aminosalicyclic acid or a pharmaceutically acceptable salt or ester thereof allow the treatment of colitis ulcerosa or Crohn's disease by oral administration. A particular slow-release tablet formation and its preparation is disclosed.

OTHER PUBLICATIONS

Gandolfo J., et al, "4-Aminosalicylic Acid Retention Enemas in Treatment of Distal Colitis", *Digestive Diseases and Sciences*, vol. 32, No. 7 (Jul. 1987), pp. 700–704.

Campieri M., et al, "A Double-Blind Clinical Trial to Compare the Effects of 4-Aminosalicylic Acid to 5-Aminosalicylic Acid in Topical Treatment of Ulcerative Colitis", Digestion 29, 1984, pp. 204–208.

Walt, R. et al, "Colitis Associated with Non-Steroidal Anti-Inflammatory Drugs", *British Medical Journal*, vol. 288, Jan. 21, 1984, p. 238.

Gilat T., et al, "Prostaglandins and Ulcerative Colitis", *Gastroenterology*, May 1979, p. 1083.

Campieri M., et al, "Prostaglandins, Indomethacin, and Ulcerative Colitis", *Gastroenterology*, Jan. 1980, p. 193.

Gould, S. et al, "Studies of Prostaglandins and Sulphasalazine in Ulcerative Colitis", *Prostaglandins and Medicine 6:* 165–182, 1981.

Rampton, D. et al, "Prostaglandin Synthesis Inhibitors in Ulcerative Colitis: Flurbiprofen Compared with Conventional Treatment", *Prostaglandins*, vol. 21, No. 3, Mar. 1981, pp. 417–425.

Rampton D., et al, "Relapse of Ulcerative Proctocolitis During Treatment with Non-Steroidal Anti-Inflammatory Drugs", *Postgraduate Medical Journal* (May 1981) 57, pp. 297–299.

Badawi A., et al, "Drug Release from Matrices Made of Polymers with Reacting Sites", *International Journal of Pharmaceutics*, 6 (1980) pp. 55–62.

PDR, 32nd Ed., 1978, pp. 310, 1699, 1700, 516–519, 682, 683, 802–805, 1438, 1439, 1077.

Rees et al, Brit. Med. J., Oct. 6, 1979, 835–836.

Martindale, The Extra Pharmacopoeia, 1972, 1766–1767.

Rasmussen et al., Gastroenterology 85: 1350-3 (1983).

Dew et al., Brit. Med. J. 287: 23–24 Jul. 2 (1983).

Brown, J. Med. Chem. 26: 1300–1307 (1983).

Dew et al., Brit. J. Clin. Pharmac. 16: 185–187 (1983).

Nielsen et al., Scand. J. Gastroenterol. 18(86): 56 (1983).

Rasmussen et al., Scand. J. Gastroenterol. 18(86): 63 (1983).

Dew et al., Brit. J. Clin. Pharmac. 17: 474–476 (1984).

Campieri et al., Abstracts of Papers: 1039 May 1984.

Selby et al., Digestion 29: 231–234 (1984).

Campieri et al., Digestion 29: 204–208 (1984).

Donald et al., Postgrad. Med. J. 61: 1047–1048 (1985).

Klotz et al., Drug. Res. 35(1): 636–637 (1985).

Habal et al., Abstracts of Papers: 1409 May 1985.

Bondesen et al., Scand. J. Gastroenterol. 21(6): 693–700 (1986).

Wolman et al., Am. J. Gastroenterol. 81(9): 877 (1986).

Saverymuttu et al., Digestion 33: 89–91 (1986).

Wellman et al., GUT 27: 814–820 (1986).

Powell-Tuck et al., Brit. Med. J. 272: 599–602 Mar. 1, 1986.

McLeod et al., Gastroenterology 90(5)(2): 1546 May 1986.

Schroeder et al., Gastroenterology 90(5)(2): 1620 May 1986.

Tremaine et al., Gastroenterology 90(5)(2): 1670 May 1986.

Guarino et al., Abstracts of Papers: 1441 May 1986.

Friedman et al., Am. J. Gastroenterology 81(6): 412–418 Jun. 1986.

Bondesen et al., Scand. J. Gastroenterol. Suppl. 21(120): 6 (1986).

Skarberg et al., Lakartidningen 63(34): 3122–3123 (1968).

Bull et al., Gastroenterology 76(3): 607–621 (1979).

Van Hees et al., GUT: 300–304 (1979).

Das et al., Gastroenterology 77: 280–284 (1979).

Molin, Acta Med. Scand. 206: 451–457 (1979).

Campieri et al., Lancet: 993 Nov. 4, 1978.

Azad Khan, Lancet: 892–895 Oct. 29, 1977.

Cowan et al., GUT 18(11): A972 (1977).

Das et al., Clinical Pharmacokinetics 1: 406–425 (1976).

Das et al., Am. J. Dig. Dis. 20(10): 971–976 (1975).

Das et al., N. Engl. J. Med. 289(10): 491–495 Sep. 6, 1973.

Das et al., GUT 14(8): 631–636 Aug. 1973.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 2 is confirmed.

New claims 3 and 4 are added and determined to be patentable.

*3. A method for the treatment of ulcerative colitis or Crohn's disease consisting essentially of orally administering an effective amount of a composition consisting essentially of free 5-aminosalicylic acid in admixture with a pharmaceutically acceptable carrier which will control the release of said effective amount of 5-aminosalicylic acid to be administered according to the actual site of said ulcerative colitis or Crohn's disease in an individual patient.*

*4. A method for the treatment of ulcerative colitis or Crohn's disease consisting essentially of orally adminsitering an effective amount of a composition consisting essentially of free 5-aminosalicylic acid in admixture with an orally administrable pharmaceutical carrier which will control the release of said effective amount of 5-aminosalicylic acid to be administered according to the actual site of said ulcerative colitis or Crohn's disease in an individual patient.*

* * * * *